US012761198B2

(12) United States Patent
Guder et al.

(10) Patent No.: US 12,761,198 B2
(45) Date of Patent: Oct. 13, 2026

(54) GAS SENSOR WITH FIRST AND SECOND ELECTRODES AND A REAGENT FOR BINDING THE TARGET GAS

(71) Applicant: BlakBear Ltd, London (GB)

(72) Inventors: Firat Guder, London (GB); Maximilian Grell, London (GB); Giandrin Barandun, London (GB)

(73) Assignee: BlakBear Ltd., London (GB)

( * ) Notice: Subject to any disclaimer, the term of this patent is extended or adjusted under 35 U.S.C. 154(b) by 439 days.

(21) Appl. No.: 18/245,522

(22) PCT Filed: Sep. 16, 2021

(86) PCT No.: PCT/EP2021/075453
§ 371 (c)(1),
(2) Date: Mar. 15, 2023

(87) PCT Pub. No.: WO2022/058413
PCT Pub. Date: Mar. 24, 2022

(65) Prior Publication Data

US 2023/0366864 A1 Nov. 16, 2023

(30) Foreign Application Priority Data

Sep. 16, 2020 (GB) ..................................... 2014604

(51) Int. Cl.
*G01N 33/00* (2006.01)
*G01N 27/07* (2006.01)
(Continued)

(52) U.S. Cl.
CPC ......... *G01N 33/0036* (2013.01); *G01N 27/07* (2013.01); *G01N 33/0073* (2013.01);
(Continued)

(58) Field of Classification Search
CPC ............... G01N 33/0036; G01N 27/07; G01N 33/0073; G01N 33/18; G01N 33/24;
(Continued)

(56) References Cited

U.S. PATENT DOCUMENTS

| | | | | |
|---|---|---|---|---|
| 6,896,781 B1 * | 5/2005 | Shen | .................. | G01N 27/4175 204/426 |
| 7,189,314 B1 * | 3/2007 | Pace | .................. | G01N 33/1886 204/412 |

(Continued)

FOREIGN PATENT DOCUMENTS

| | | | | |
|---|---|---|---|---|
| CN | 105980849 A * | 9/2016 | ........... | G01N 27/127 |
| GB | 2202948 A | 10/1988 | | |

(Continued)

OTHER PUBLICATIONS

Burton Lamar et al: "Review—The "Real-Time" Revolution for In situ Soil Nutrient Sensing", Journal of the Electrochemical Society, vol. 167, Feb. 17, 2020.

(Continued)

*Primary Examiner* — Fatemeh Esfandiari Nia
(74) *Attorney, Agent, or Firm* — Adam Warwick Bell; Matthew Rupert Kaser

(57) ABSTRACT

A gas sensor for sensing a target gas, the gas sensor comprising first and second electrodes; a support layer between the first and second electrodes; and a reagent on the support layer for binding the target gas, wherein the first and second electrodes are in electrical contact with the support layer and the reagent.

15 Claims, 17 Drawing Sheets

(51) Int. Cl.
*G01N 33/18* (2006.01)
*G01N 33/24* (2006.01)
*G01N 33/49* (2006.01)
*G01N 33/493* (2006.01)

(52) U.S. Cl.
CPC ............. *G01N 33/18* (2013.01); *G01N 33/24* (2013.01); *G01N 33/49* (2013.01); *G01N 33/493* (2013.01)

(58) Field of Classification Search
CPC .... G01N 33/49; G01N 33/493; G01N 33/245; G01N 27/02; G01N 27/06; G01N 33/004; G01N 33/0052; G01N 33/1813; G01N 33/182
See application file for complete search history.

(56) References Cited

U.S. PATENT DOCUMENTS

| | | | | |
|---|---|---|---|---|
| 10,495,592 | B1 | 12/2019 | Peterson et al. | |
| 2003/0148530 | A1* | 8/2003 | Lauks | G01N 33/49 436/811 |
| 2006/0081032 | A1* | 4/2006 | Brinz | G01N 27/125 73/23.31 |
| 2008/0116908 | A1 | 5/2008 | Potyrailo et al. | |
| 2009/0119041 | A1* | 5/2009 | Hu | G01N 33/2823 702/65 |
| 2010/0022731 | A1* | 1/2010 | Ryan | C08F 26/06 526/263 |
| 2012/0067744 | A1 | 3/2012 | Vincent | |
| 2017/0205383 | A1 | 7/2017 | Lu et al. | |
| 2019/0067585 | A1* | 2/2019 | Momose | G01N 27/125 |
| 2019/0216359 | A1* | 7/2019 | Chuang | G01N 33/48707 |
| 2019/0257829 | A1* | 8/2019 | Ludwig | G01N 33/54373 |
| 2020/0124554 | A1* | 4/2020 | Zhao | G01N 27/06 |
| 2022/0365059 | A1* | 11/2022 | Tarpeh | G01N 33/18 |

FOREIGN PATENT DOCUMENTS

| | | | | |
|---|---|---|---|---|
| GB | 2509127 | A | 6/2014 | |
| WO | 9322668 | A1 | 11/1993 | |
| WO | WO-2018216017 | A1 * | 11/2018 | G01N 27/127 |
| WO | WO-2020240125 | A1 * | 12/2020 | G01F 23/268 |

OTHER PUBLICATIONS

Giandrin Barandun et al: "Cellulose Fibers Enable Near-Zero-Cost Electrical Sensing of Water-Soluble Gases", ACS Sensors, May 8, 2019 (May 8, 2019), pp. A-h.

Grell Max et al: "Determining and Predicting Soil Chemistry with a Point-of-Use Sensor Toolkit and Machine Learning Model", bioRxiv, Oct. 9, 2020.

Maity Avisek et al: "High sensitivity NH3 gas sensor with electrical readout made on paper with perovskite halide as sensor material", Scientific Reports, vol. 9, No. 1, Dec. 1, 2019.

Rogovska Natalia et al: "Development of field mobile soil nitrate sensor technology to facilitate precision fertilizer management", Precision Agriculture, Springer US, Boston, vol. 20, No. 1, May 14, 2018 (May 14, 2018), pp. 40-55.

"European Examination Report", issued in the counterpart European Application 21 777 763.0, dated Feb. 4, 2025.

Lianghui Huang, Peng Jiang, Dong Wang, Yuanfang Luo, Mufang Li, Hoseon Lee, Rosario A. Gerhardt, "A novel paper-based flexible ammonia gas sensor via silver and SWNT-PABS inkjet printing", Sensors and Actuators B: Chemical, vol. 197, 2014, pp. 308-313, ISSN 0925-4005, https://doi.org/10.1016/j.snb.2014.02.081.

Shen W-C, Shih P-J, Tsai Y-C, Hsu C-C, Dai C-L. "Low-Concentration Ammonia Gas Sensors Manufactured Using the CMOS-MEMS Technique". Micromachines. 2020; 11(1):92. https://doi.org/10.3390/mi11010092.

* cited by examiner

GAS SENSOR WITH FIRST AND SECOND ELECTRODES AND A REAGENT FOR BINDING THE TARGET GAS

The present disclosure relates to a gas sensor and a method of sensing a gas.

Point-of-use (PoU) gas sensors find use in a broad range of applications where gas concentration readings are required quickly or in a remote location. As such, there is a need for more accurate, reliable and cost effective PoU gas sensors for different gases.

Soil is an example of a natural medium that is highly complex physically, chemically and biologically, but where straightforward and practical guidance is required to sustain human life. The global population boom that began in the 1960s resulted in surging increase in nitrogen fertilization to supply the required crop yields. Overfertilization has damaged soil health and yields are declining, while the population continues to rise. Most farmers across the world have no way to measure their fertilizer requirements, so practical guidance leans toward overfertilization, to maximise yields. Either food consumption must reduce, or farming technology and practices must change, because soil degradation is not sustainable.

Even in developed countries where farmers have access to laboratory sampling, soil nitrogen changes faster than the sampling time, so measurements are not useful to guide fertilization. As such, there is a particularly pressing need for PoU sensors for quickly and accurately determining soil nitrogen levels. This would greatly help farmers, with little or zero access to soil measurements, to measure crucial soil nutrients with enough accuracy to reduce overfertilization or improve crop yields.

Aspects of the disclosure are set out in the independent claims and optional features are set out in the claims dependent thereon.

In a first aspect, a gas sensor for sensing a target gas is provided, the gas sensor comprising: first and second electrodes; a support layer between the first and second electrodes; and a reagent on the support layer for binding the target gas, wherein the first and second electrodes are in electrical contact with the support layer and the reagent. The reagent may be termed a scrubbing reagent.

In use, when the gas sensor is exposed to the target gas, the target gas is bound by the reagent. This changes the impedance of the support layer/reagent between the first and second electrodes. This change in impedance can be measured and used to determine the concentration or presence of the target gas. The support layer may be porous and/or hygroscopic.

Each electrode may be carbon based. For example, each electrode may be made of carbon ink, glassy carbon, graphite, graphene or carbon black. Each electrode may be metallic. For example, each electrode may be made of a noble metal such as silver, gold, platinum or iridium. Alternatively the electrodes may be made of conductive polymer. Each electrode may be deposited onto the support layer, for example, by evaporation, sputtering or printing, such as screen printing. The first and second electrodes may be interdigitated. The gas sensor may further comprise first and second electrical contacts, respectively connected to the first and second electrodes for connecting the first and second electrodes to a voltage source.

The support layer may be made of a cellulosic material, such as paper, such as filter paper. Alternatively, the support layer may be made of a textile, a fabric, a polymer, a mesh or any other suitable material. The support layer may be micro or nanoporous and/or any hygroscopic material. A wax barrier, for controlling or limiting the spread of the reagent, may surround the electrodes.

The support layer with reagent may be termed a scrubber or gas scrubber. As is well known to the skilled person, a scrubber is a device or structure for capturing, reacting, binding, adsorbing or absorbing a gas. The reagent is a chemical, compound or material that binds or captures the target gas, for example by chemical or physical means, for example by reacting with the gas, solvating the gas, adsorbing the gas or absorbing the gas. The reagent may be in an aqueous solution.

The gas sensor may further comprise a voltage source, wherein the voltage source is configured to apply an electrical potential between the first and second electrodes. An electrical potential may also be termed a voltage or potential bias. The voltage source may be an alternating voltage source. The electrical potential may be an alternating potential. The frequency of the alternating potential may be 1 Hz-1 kHz. The amplitude of the electrical potential may be 1-10 V. Other frequencies and voltages may be used.

The gas sensor may further comprise or be connected to an electronic controller. The controller may be configured to control the electrical potential and/or perform one or more of the steps of the methods of sensing a target gas or measuring the concentration of ions in a sample discussed below. For example, the controller may be configured to perform one of more of: modifying the electrical potential, amplifying signals, digitizing signals, measuring the impedance of the support layer/reagent at one or more times, calculating a rate of change of impedance, and determining a concentration of the target gas or of target ions in a sample based on impedance measurements, for example by comparing impedance measurements with calibration data.

The target gas may be an alkaline gas and the reagent acidic. An alkaline gas is a gas that may accept a hydrogen ion and/or donate an electron pair and/or, when dissolved in water, has a pH greater than 7. An acidic reagent may donate a hydrogen ion and/or accept an electron pair and/or has a pH less than 7 in solution. The reagent may be in solution and may have a concentration equal to or greater than 1 μM, 1 mM, 0.1 M or 1 M. The acidic reagent may be an acid, such as a strong acid, such as sulphuric acid, nitric acid or hydrochloric acid. The target gas may be ammonia or an alkyl amine, for example any alkyl amine that is gaseous at 25 °C and 1 atm. Alkyl amines include trimethylamine and dimethylamine. When the target gas is ammonia, a preferred acidic reagent is sulphuric acid.

Alternatively, the target gas may be an acidic gas and the reagent alkaline. An acidic gas is a gas that may donate a hydrogen ion and/or accept an electron pair and/or, when dissolved in water, has a pH less than 7. An alkaline reagent may accept a hydrogen ion and/or donate an electron pair and/or has a pH greater than 7 in solution. The reagent may be in solution with a concentration equal to or greater than 1 μM, 1 mM, 0.1 M or 1 M. The reagent may be an alkali, such as a metal hydroxide, such sodium hydroxide, potassium hydroxide or calcium hydroxide. The target gas may be carbon dioxide, hydrogen fluoride, hydrogen chloride, hydrogen bromide or hydrogen iodide. When the target gas is carbon dioxide, a preferred alkaline reagent is a metal hydroxide such as sodium hydroxide.

The gas sensor may be a device for determining a quantity of target ions in a sample, the gas sensor further comprising a container for receiving the sample, wherein the container is fluidically connected to the gas sensor. The inside of the container and gas sensor may be sealed, for example from an ambient atmosphere, for example using a lid. The seal may be a gas-tight seal. The container may connect to the gas sensor via a push or screw fit, or by any other suitable means.

In use, a reagent, such as an acidic or alkaline solution, which may be termed a sample solvent, sample activating solution or sample activating reagent, is added to a sample in the container. The reagent converts the target ions into a gaseous species (the target gas) which is released into the container (the gaseous species may be dissolved in the solution before diffusing to the surface of the solution and escaping as a gas). The gaseous species/target gas then migrates through the container to the support layer, is bound by the reagent, and changes the impedance of the support layer/reagent between the first and second electrodes. The change in impedance can be measured and used to determine the concentration of ions in the original sample. Advantageously, the gas sensor eliminates matrix effects due to a complex sample.

The target ions in the sample may be ammonium ions, alkylammonium ions, fluoride ions, chloride ions, bromide ions, iodide ions or bicarbonate ions. The concentration of ions in the sample may be at least 0.01 ppm, preferably at least 0.1 ppm and more preferably at least 1 ppm. The ions in the sample may be in equilibrium with non-ionic forms and/or may be hydrated. The ions in the sample are ions that can be converted into gaseous molecules (either free gaseous molecules or solvated gaseous molecules) by the sample activating reagent. The ratio between free gaseous molecules in the container and solvated molecules is determined by the partial pressure of free gaseous molecules in the container, in accordance with Henry's law. The solvated gaseous molecules may also be in equilibrium with a corresponding solvated ionic species, for example if the gaseous molecules can accept or donate hydrogen ions in water. The balance of this equilibrium may be dependent on a pH of the sample/sample activating solution. Advantageously, since the reagent binds the target gas, it draws the target gas out of the sample container. This reduces the partial pressure of the target gas in the sample chamber, which in turns draws more of the target gas out of the sample/sample activating solution, which in turn causes a solvated ionic form of the target gas (if present) to be converted into the non-ionic gaseous form. For example, solvated aqueous ammonium ions exist in equilibrium with solvated ammonia molecules, which in turn are in equilibrium with surrounding gaseous ammonia. The equilibrium between solvated ammonia ions and solvated ammonia is dependent upon the pH of the sample/sample activating solution. A more alkaline pH pushes the equilibrium towards ammonia. Conversely, a more acidic pH pushes the equilibrium towards ammonium.

The sample may be soil, agricultural run-off, river water, sea water, sewage, blood, urine or an extract of any of these. The sample may be any chemical or biological sample. The concentration of target ions in the sample, particularly in the case of ammonium ions, may be at least 0.01 ppm, preferably at least 0.1 ppm and more preferably at least 1 ppm. Advantageously, soil ammonium concentration may be used to estimate soil nitrate levels using machine learning algorithms, as discussed herein.

The container may contain or be fluidically connected to a reagent for converting the target ions in the sample into the target gas. That is, the reagent may be provided in a vessel containing the reagent, or be connected to vessel containing the reagent. The reagent may be a basic or acidic solution. The basic solution may comprise a base, such as a metal hydroxide, such a sodium hydroxide, potassium hydroxide or calcium hydroxide. The concentration of the base may be at least 0.01 M, preferably at least 0.1 M and more preferably at least 1 M. The acidic solution may comprise an acid, such as sulphuric acid, nitric acid or hydrochloric acid. The concentration of the acid may be at least 0.01 M, preferably at least 0.1 M and more preferably at least 1 M. The sample activating reagent may be contained in a syringe or device for injection of the reagent into the container. The reagent may be sealed in the syringe or device, for example with a chemically resistant seal. Alternatively or additionally, the reagent may be contained within a pouch, capsule or blister pack, each of which may be configured to release the reagent into the container.

In a preferred embodiment, the sample is soil extract, the ions are ammonium ions and the container contains a sodium hydroxide solution. Advantageously, such a device for measuring ammonium ions in soil is particularly robust to weather conditions, soil type and technical ability of the user.

In an aspect, a method of determining a concentration of a target gas is provided, the method comprising: exposing a gas sensor described above to a gas sample comprising the target gas, such that the target gas is bound by the reagent; measuring an impedance of the support layer by applying an electrical potential between the first and second electrodes at a first time; measuring an impedance of the support layer by applying an electrical potential between the first and second electrodes at a second time; and determining the concentration of the target gas based on the impedance at the first time and the impedance at the second time.

The concentration of the target gas may be measured in parts-per notation, for example parts per million, as a partial pressure, a percentage weight, a percentage volume, a number of moles per unit volume or a number of moles per unit mass. The method may further comprise measuring a rate of change in impedance. The method may further comprise measuring the impedance at one or more further times between the first time and the second time, for example by continuously monitoring the impedance between the first time and the second time. The change in impedance may be an increase in impedance. The method may further comprise using and or training a predictive machine learning model on short measurement times between the first and second times. Determining the concentration of the target gas based on the impedance at the first time and the impedance at the second time may comprise comparing: i) the rate of change in impedance after a fixed time, or ii) the time when the rate of change falls below a threshold rate of change, with a calibration curve or list of calibration results, for example by interpolating between two calibration results of the list of calibration results. The method may further comprise preparing a calibration curve or list of calibration results, for example by measuring i) an impedance of the support layer at a first time and the impedance at a second time; ii) the rate of change after a fixed period of time; or iii) the time taken for rate of change to drop below a threshold value, for at least two known target gas concentrations. Advantageously, the method could be used to detect, for example, a gas leak.

In an aspect, a method of determining a concentration of target ions in a sample using a gas sensor is provided, wherein the gas sensor is a gas sensor comprising a container as described above, the method comprising: inserting the sample into the container; mixing the sample with a reagent for converting the target ions in the sample into the target gas, thereby releasing the target gas into the container; measuring an impedance of the support layer by applying an electrical potential between the first and second electrodes at a first time; measuring an impedance of the support layer by applying an electrical potential between the first and second electrodes at a second time; and determining the concentration of ions in the sample based on the impedance at the first time and the impedance at the second time.

For the above methods, the reagent may be the same as any sample activating reagent described above. The target ions and target gas may be the same as any target ions and target gas described above. The sample may be the same as any sample described above. The concentration of target ions may be measured in parts-per notation, for example parts per million, as a percentage weight, a percentage volume, a number of moles per unit volume or a number of moles per unit mass.

The method may further comprise sealing the device after mixing the sample with the solution. The method may further comprise measuring a rate of change in impedance. The method may further comprise measuring the impedance at one or more further times between the first time and the second time, for example by continuously monitoring the impedance between the first time and the second time. The method may further comprise using and or training a predictive machine learning model on short measurement times between the first and second times. Determining the concentration of the target ions based on the impedance at the first time and the impedance at the second time may comprise comparing: i) the rate of change in impedance after a fixed time; or ii) the time when the rate of change falls below a threshold rate of change, with a calibration curve or list of calibration results, for example by interpolating between two calibration results of the list of calibration results. The method may further comprise preparing a calibration curve or list of calibration results, for example by measuring i) an impedance of the support layer at a first time and the impedance at a second; ii) the rate of change after a fixed period of time; or iii) the time taken for rate of change to drop below a threshold value, for at least two known target ion concentrations for a given sample. In a preferred embodiment, the sample is soil extract, the ions are ammonium ions and the container contains a sodium hydroxide solution.

Advantageously, using these methods, farmers can instantly determine crucial soil nutrients using only robust PoU measurements. This approach could enable precision farming of a new calibre, reducing fertilizer requirements, soil degradation and eutrophication, while improving crop yields.

Embodiments will now be described by way of example with reference to the drawings of which:

DETAILED DESCRIPTION—FIGURE REFERENCES

Figure 1:
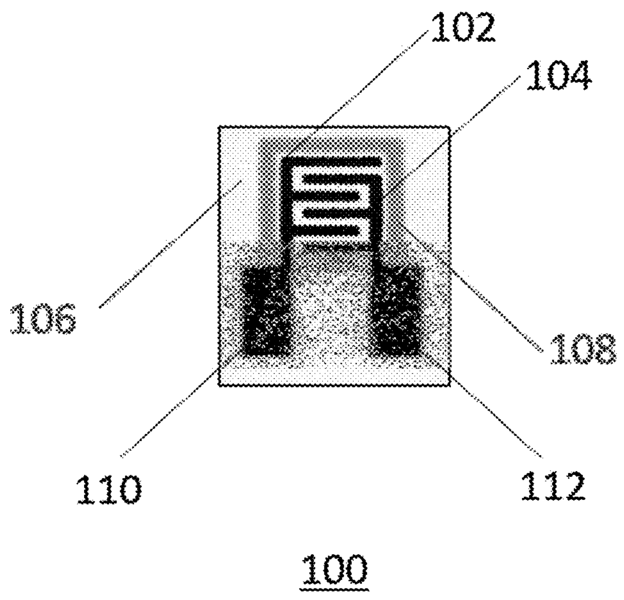
FIG. 1 illustrates a gas sensor for measuring ammonia concentration.

With reference to FIG. 1, in a first embodiment, a gas sensor 100 for sensing ammonia gas comprises first and second interdigitated carbon electrodes 102/104 (No. C2130925D1 conductive carbon ink, 55/45 wt % with No. S60118D3 diluent from GWENT Group) screen printed onto a chromatography paper support layer 106 (Whatman™, grade 1 chromatography paper, 20 cm×20 cm, 0.18 mm thickness). The electrodes are dried overnight at room temperature to remove excess organic solvents from the electrodes. The design of the electrodes consists of three interdigitated electrodes with 1 mm spacing between each finger. First and second electrode contacts 110/112, also printed carbon ink, respectively connect to the first and second electrodes 102/104 and are used to connect the first and second electrodes to a voltage source when the sensor is in use, to apply an electrical potential between the first and second electrodes.

Figure 9:
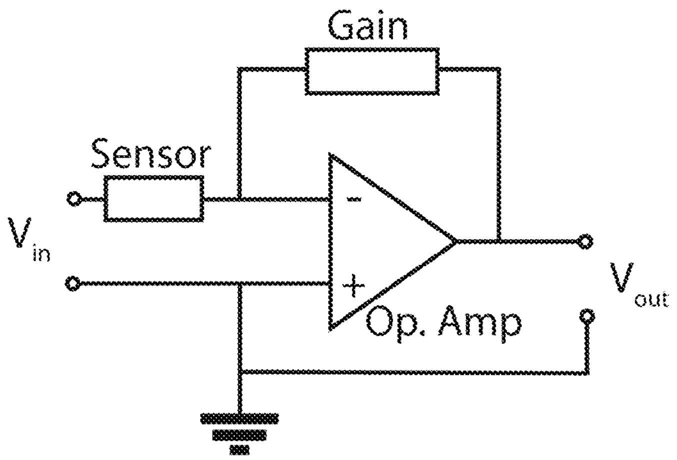
FIG. 9 illustrates a schematic showing electronics for measuring ionic impedance.

In use, the sensor of the first and second embodiments is connected to an electronic controller. The controller is configured to apply an alternating electrical potential (10 Hz, 4 V amplitude peak-to-peak) between the first and second electrodes and measure the impedance of the support layer 106. This can be achieved using conventional means well known to the skilled person, for example as illustrated in FIG. 9, which is a schematic showing electronics for measuring ionic impedance.[27] An alternating voltage is supplied (Vin) across the electrodes, and the current passing through measured as a voltage (Vout) with a transimpedance amplifier (implemented with an Operational Amplifier), amplified with a resistor (Gain). There is an increase in ionic impedance (decrease in ionic conductivity) during neutralization of the reagent as the target gas contacts the reagent (i.e. the sulphuric acid is neutralised by ammonia in the first embodiment or the sodium hydroxide is neutralised by carbon dioxide in the second embodiment). As the neutralization of the reagent proceeds, the impedance increases. Thus, a change in impedance is indicative of the presence of the target gas (the concentration of the gas need not be determined) and the sensor may be used to determine the presence of the target gas. Alternatively, the concentration of the target gas may be determined in accordance with the following method.

Figure 2:
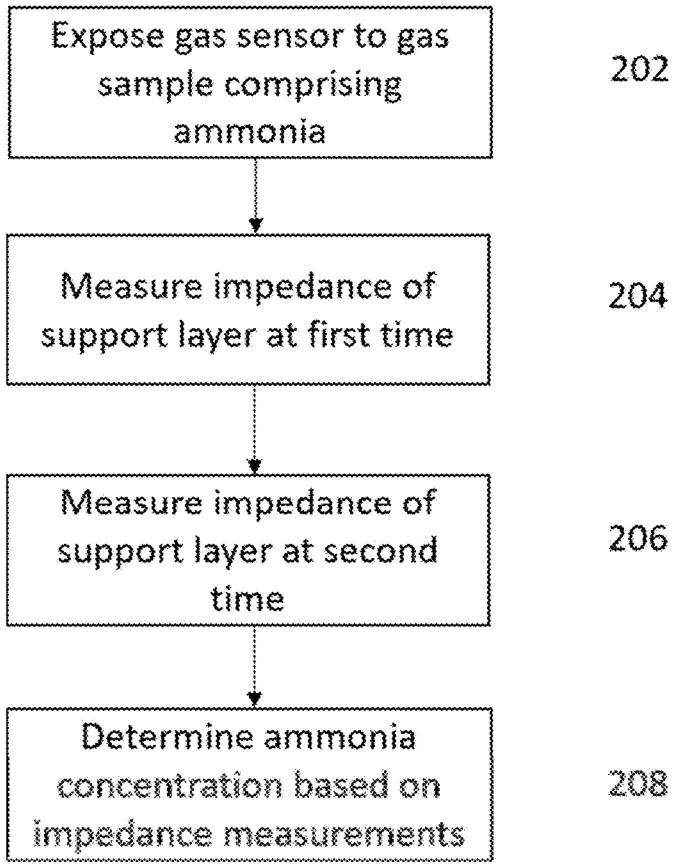
FIG. 2 is a flow diagram for a method of using the gas sensor of FIG. 1.

FIG. 2 is a flow diagram for a method of determining a concentration of ammonia gas using the gas sensor of the first embodiment. The method comprises exposing 202 the gas sensor 100 of the first embodiment to a gas sample comprising ammonia. The ammonia is bound by the reagent, changing the impedance of the reagent/support layer 106. The impedance of the support layer 106 is measured 204 by applying an electrical potential between the first and second electrodes 102/104 at a first time. The impedance of the support layer 106 is then measured 206 again by applying an electrical potential between the first and second electrodes 102/104 at a second time. The concentration of ammonia is then determined 208 based on the impedance at the first time and the impedance at the second time. This is achieved by calculating the rate of change of impedance from the first and second impedance measurements. If the rate of change is below a threshold rate of change, it is determined that the reagent is neutralised and the time taken for neutralisation is converted into an ammonia concentration using a calibration curve prepared by measuring the neutralisation time for a range of known ammonia concentrations (previously measured using the gas sensor-a new gas sensor must be used each time). Other ways of determining the ammonia concentration from the impedance measurements are possible, such as determining the rate of change of impedance after a fixed period of exposure of the gas sensor to the target gas, and comparing this with a corresponding calibration curve. This method may also be used to measure carbon dioxide concentration using the gas sensor 100 of the second embodiment, mutatis mutandis.

FIG. 3*i* illustrates a third embodiment of a gas sensor 100 for determining a quantity of ammonium ions in a soil sample extract. The gas sensor 100 of the first embodiment, further comprises a chemically inert 50 ml VWR centrifuge tube container 114 with a gas-tight screwcap lid 116. The container 114 and lid 116 are chemically inert. First and second wires 118/120 pass through the lid 116 and connect to the first and second electrode contacts 110/112 of the gas sensor 100, respectively. 1 ml of 15 M sodium hydroxide solution 122 is provided in the bottom of the container 114. As illustrated in FIG. 3*i*, in use, an aqueous soil sample extract, comprising ammonium ions, is mixed with the solution 122, releasing ammonia gas into the headspace of the container. The ammonia neutralises the sulphuric acid reagent, changing the impedance of the support layer 106, as is the case with the first embodiment. The change in impedance can then be used to determine the ammonium concentration in the soil sample extract, for example using the method below. Instead of soil extract, the sample can be any sample comprising ammonium ions, including agricultural run-off, river water, sea water, sewage, blood, urine, or an extract of any of these.

Figure 4:
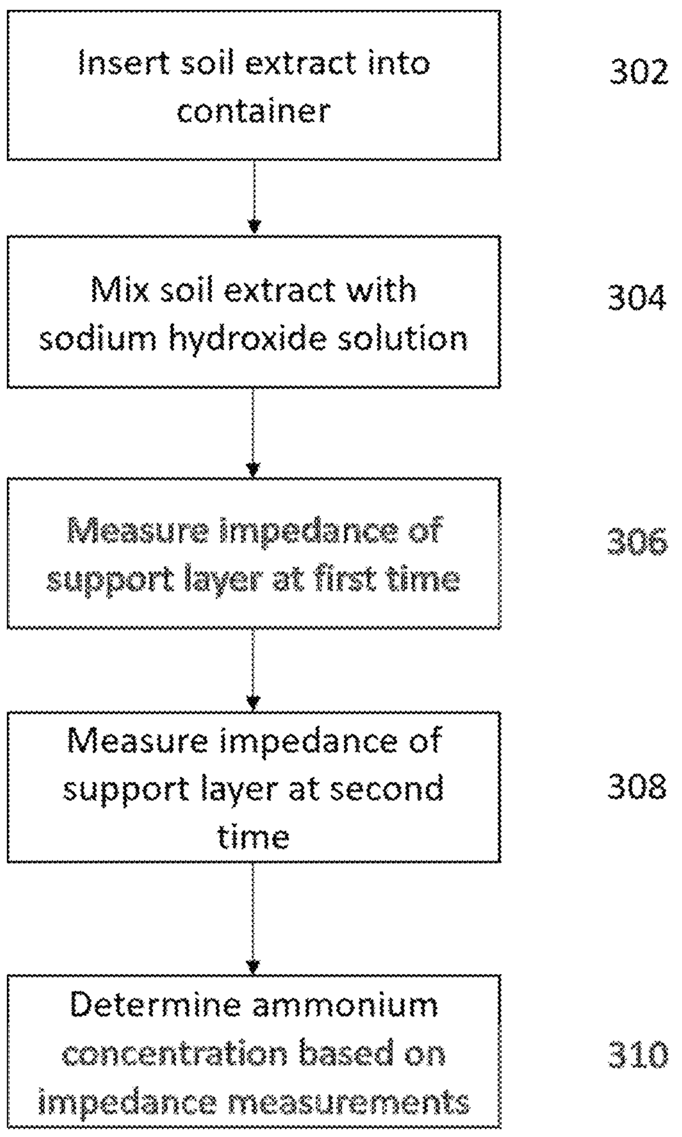
FIG. 4 is a flow diagram for a method of using the gas sensor of FIG. 3.

FIG. 4 is a flow diagram for a method of determining the concentration of ammonium ions in a soil sample extract using a gas sensor 100, wherein the gas sensor 100 is the gas sensor 100 of the third embodiment. First, the sample is inserted 302 into the container 114. The sample is then mixed 304 with a 15 M sodium hydroxide solution 122 for converting the ammonium ions in the sample into ammonia, thereby releasing ammonia into the headspace of the container 114, where the ammonia diffuses up to the support layer 106 and neutralises the sulphuric acid reagent. The impedance of the support layer is then measured 306 by applying an electrical potential between the first and second electrodes at a first time, and measured 308 again in the same way at a second time. The concentration of ions in the sample is then determined 310 based on the impedance at the first time and the impedance at the second time, as discussed below.

Figure 8:
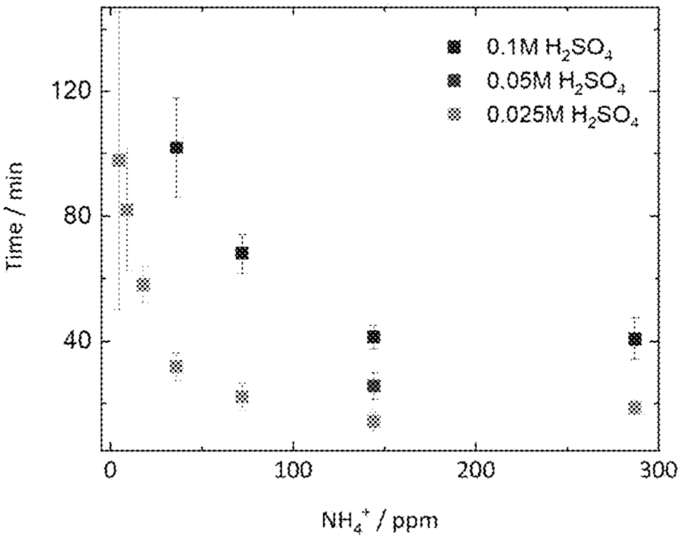
FIG. 8 illustrates calibration curves for ammonium nitrate in water.

This method has a limit of detection of 3+1 ppm ammonium, up to at least 144 ppm. FIG. 8 shows calibration curves for ammonium nitrate in water (no soil), which verify that the soil measurements are from ammonium alone. Sensing of ammonia with the sensor 100 may be susceptible to interferences from other water-soluble alkaline gases; however, because ammonia has the highest water solubility and is the dominant water-soluble alkaline gas species in common soil samples due to the presence of fertilizer (ammonium nitrate), the signal generated by the sensor 100 largely originates from ammonium. In detail, the soil sample extract is created by pressing 100 ml deionized water through 100 g of soil. A 5 ml soil solution is injected into the container 114. In the container 114, the solubilized soil-ammonium is in equilibrium with solubilized ammonia (Equation 1), which is in equilibrium with volatilized ammonia in the headspace of the container under Henry's law (Equation 2).

The pH is increased to 14 when mixed with the concentrated sodium hydroxide solution 122, shifting the equilibrium toward $NH_{3(aq)}$ and ultimately $NH_{3(g)}$. The ammonia in the headspace of the container once again dissolves in the sulphuric acid on the support layer 106, for example as described in Barandun et. al.,[27] and then neutralizes the sulphuric acid causing an increase in the ionic impedance (presumably due to the neutralization of highly mobile $H^+$ ions) of the support layer 106 in a concentration dependent manner (see FIG. 3*ii*). Neutralization of volatilized ammonia (Equation 3) draws out more ammonium from the soil extract to maintain equilibrium, hence the reagent on the support layer 106 acts as a scrubber of soil-ammonium.

There is a decrease in ionic impedance during neutralization, which is measured electrically.[27] An alternating voltage (10 Hz, 4 V amplitude peak-to-peak) is supplied across the electrodes 102/104 via wires 118/120 (discussed in further detail below), and the current passing through measured as a voltage with a transimpedance amplifier, amplified with a gain resistor (see FIG. 9). As the neutralization continues, the impedance of the paper increases slowly and the time it takes to complete or slow dramatically used as the analytical signal shown in FIG. 3*iii* (the analytical signal is circled in red and the error shown in grey (calculated by standard deviation of n−5 measurements; see FIG. 10 for raw data). This may be determined by determining the time taken for the rate of change in impedance to drop below a threshold level. In this instance, the time used as analytical signal was A) when the gradient was zero or B) when there was a step change in gradient (>80% change in <10 minutes), which ever happened sooner. Before measuring unknown concentrations, the sensor is calibrated in a range of concentrations of ammonium from 4.5-144 ppm, in soil fertilized with ammonium nitrate; the calibration curve (log-log) is shown in FIG. 3*iv*. The inventors' measurements of ammonium concentration were compared to external laboratory measurements with a score of $R^2$=0.85 (FIG. 11). A calibration curve for ammonium nitrate in water (no soil) was also measured, to verify the soil measurements are indeed from ammonium alone (FIG. 8).

The method of FIG. 4 can also be used with the gas sensor of the fourth embodiment to measure bicarbonate ions in a sample, mutatis mutandis.

In this work a new and quick approach is demonstrated for determining crucial, but difficult to measure N-levels in soil. A new type of gas-phase $NH_4^+$ sensor (of the third embodiment above), simulated climate data (i.e. rainfall and temperature) and off-the-shelf soil pH and conductivity sensors are combined with a statistical machine learning model to instantaneously and accurately determine levels of $NO_3^-$ in soil. It is demonstrated that the N-levels in soil can also be predicted into the future using a long short-term memory recurrent neural network over a 12-day period. With this new approach (FIG. 5), fertilization can be provided more precisely to improve yields, while preventing over fertilization, thus environmental degradation.

Figure 5:
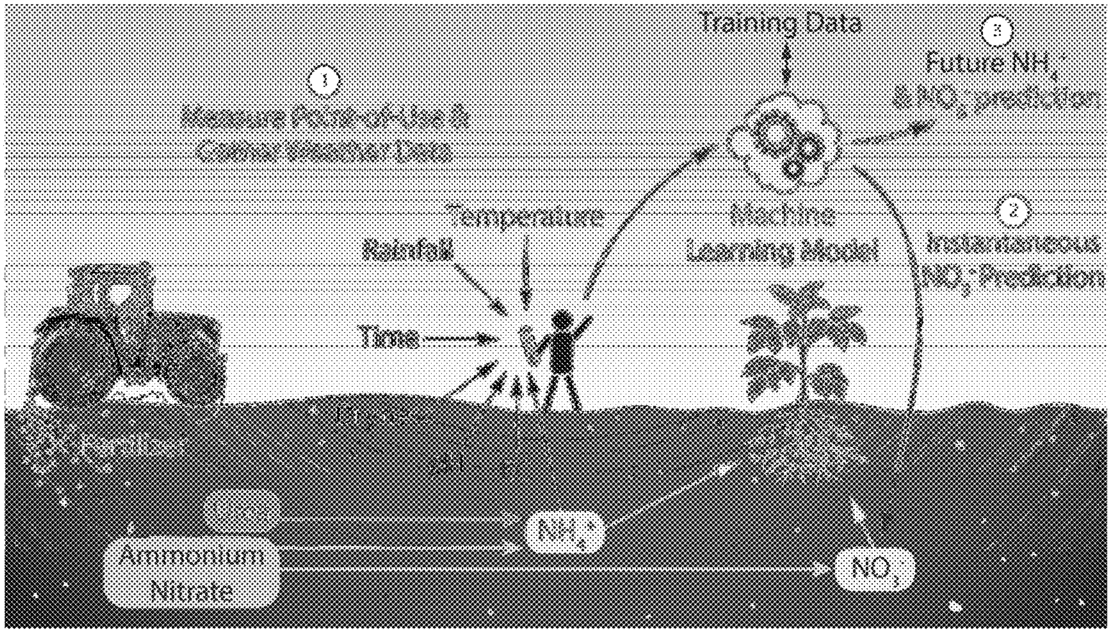
FIG. 5 illustrates an approach to determining nitrogen levels in soil.

With reference to FIG. 5, nitrogen fertilizer is the backbone of modern agriculture, and is typically applied as urea or ammonium nitrate, fuelling the soil-nitrogen cycle. This outputs solvated $NH_4^+$ and $NO_3^-$, which are strongly taken up by plant roots. POU electrical measurements (including a new soil-$NH_4^+$ sensor disclosed above) are combined with a machine learning model to quantify difficult-to-measure soil nutrients (such as $NO_3^-$) and forecast them into the future. This provides real-time dynamic soil nitrogen information to guide fertilization—reduce over-fertilization, understand the effect of weather, and ensure enough plant-available nitrogen to maximise crop yield—without laboratory measurements. At scale, this model could use a bare minimum of readily available input data to quantify and predict crucial outputs (e.g. soil macronutrients) in highly complex systems (such as soil).

Figure 6:
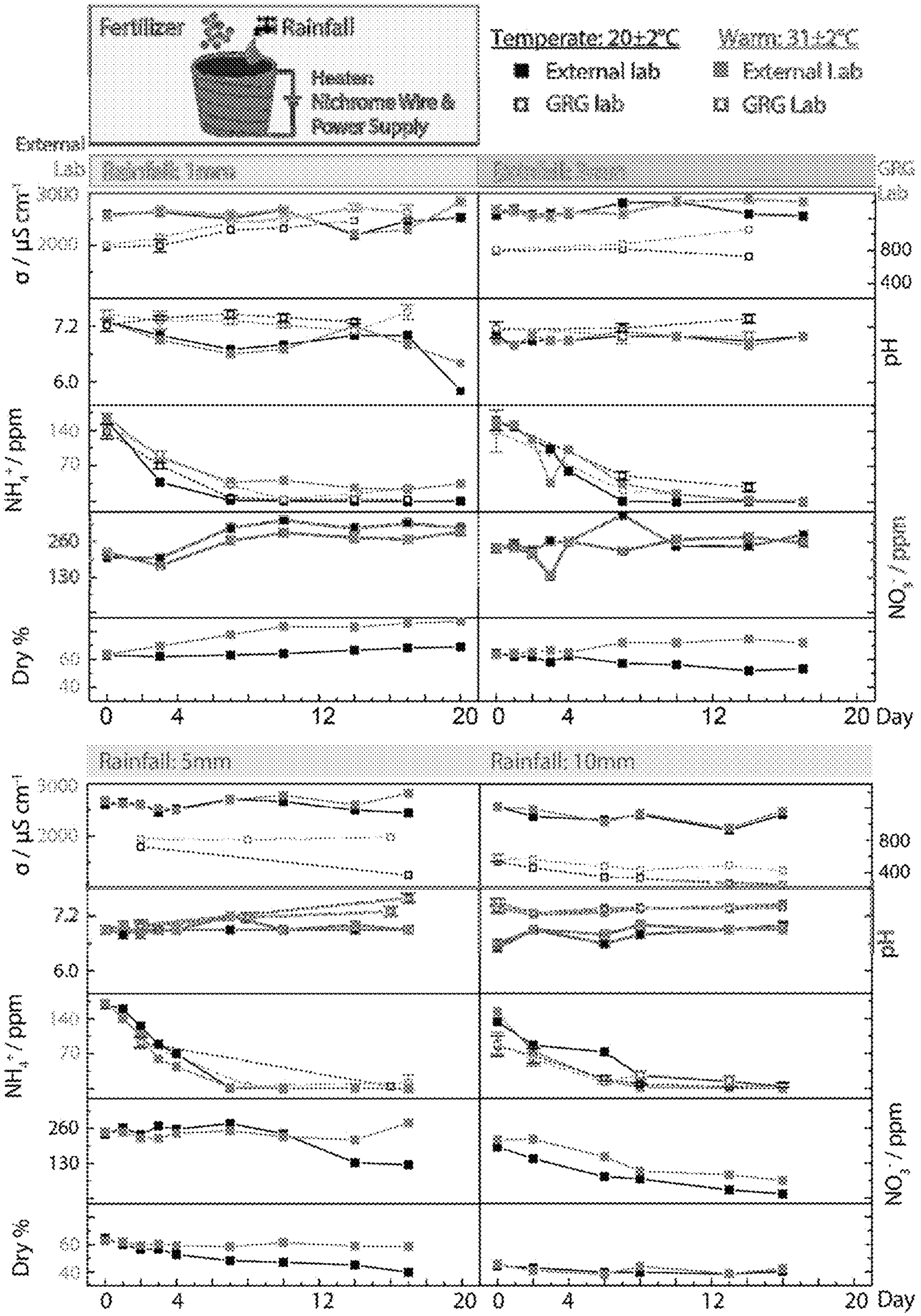
FIG. 6 illustrates time series data concerning dynamics of soil nitrogen.

Understanding how nitrogen species evolve after fertilization, in particular the nitrification from $NH_4^+$ to $NO_3^-$, is important to growers for tailoring fertilization to climatic conditions and crop types, while reducing losses and environmental damage[28]. Time series data concerning dynamics of soil nitrogen were collected over short timescales (<20 days) in experiments simulating soil in a field (FIG. 6). To reduce complexity, no plants were grown and the nitrogen dynamics only due to microbial activity, run-off and volatilization (escape of $NH_{3(g)}$) were investigated. 5.1 kg of soil (Westland Top Soil) were placed in 15 L plastic pots and stored in the laboratory without covering their tops. In each experiment, the environmental conditions were controlled in two ways: i) adding a controlled amount of water to simulate rainfall, ii) passing an electrical current through a resistive heating wire (nichrome wire), wrapped around the containers, to control temperature uniformly. The soil type (sandy loam, sieved) and amount of fertilizer added were kept fixed for all experiments (fertilizer $NH_4NO_3$ was added in the beginning of each experiment to produce a concertation of 120 ppm, approximately equal to 241 kg/ha of $NH_4NO_3$ or 85 kg/ha nitrogen—calculation in SI). Experiments were performed for eight sets of environmental conditions spanning arid (1 mm/day rainfall) to tropical (10 mm/day rainfall) with temperatures ranging from 19-21° C. (temperate) to 26-34 °C (warm). Measurements of soil temperature, rainfall, pH, electrical conductivity (EC) and $NH_4^+$ were made in the inventors' laboratory (Güder Research Group—GRG). Levels of pH, EC, $NH_4^+$ were also measured in an external laboratory (NRM, Cawood Scientific), in addition to dryness and $NO_3^-$, for comparison and training of the machine learning model. Although when building the machine learning model the dryness values provided by the commercial laboratory were relied upon, dryness is highly correlated with rainfall and temperature (in the inventors' dataset, temperature and rainfall predict dryness using linear regression with $R^2$=0.86, see FIG. 12 and the equation in the SI) hence can be estimated using these two metrics without needing further analytical measurements.

With reference to FIG. 6, Time series data of soil nitrogen dynamics were measured over short timescales (<20 days), where each corresponds to soil under different environmental conditions. Rainfall and temperature were controlled by adding a controlled amount of water, and passing current through a resistive heating wire (top of FIG. 6). Environmental conditions span arid (1 mm rain/day) to tropical (10 mm rain/day), temperate (19-21 °C) and warm (26-34 °C). Initial fertilization with $NH_4NO_3$ was fixed at 120 ppm. Measurements of soil temperature, rainfall, pH, EC and $NH_4^+$ were made in the inventors' laboratory (GRG), and pH, EC, dry %, $NH_4^+$ and $NO_3^-$ were measured in an external laboratory (NRM) for comparison and training the machine learn model.

Figure 3:
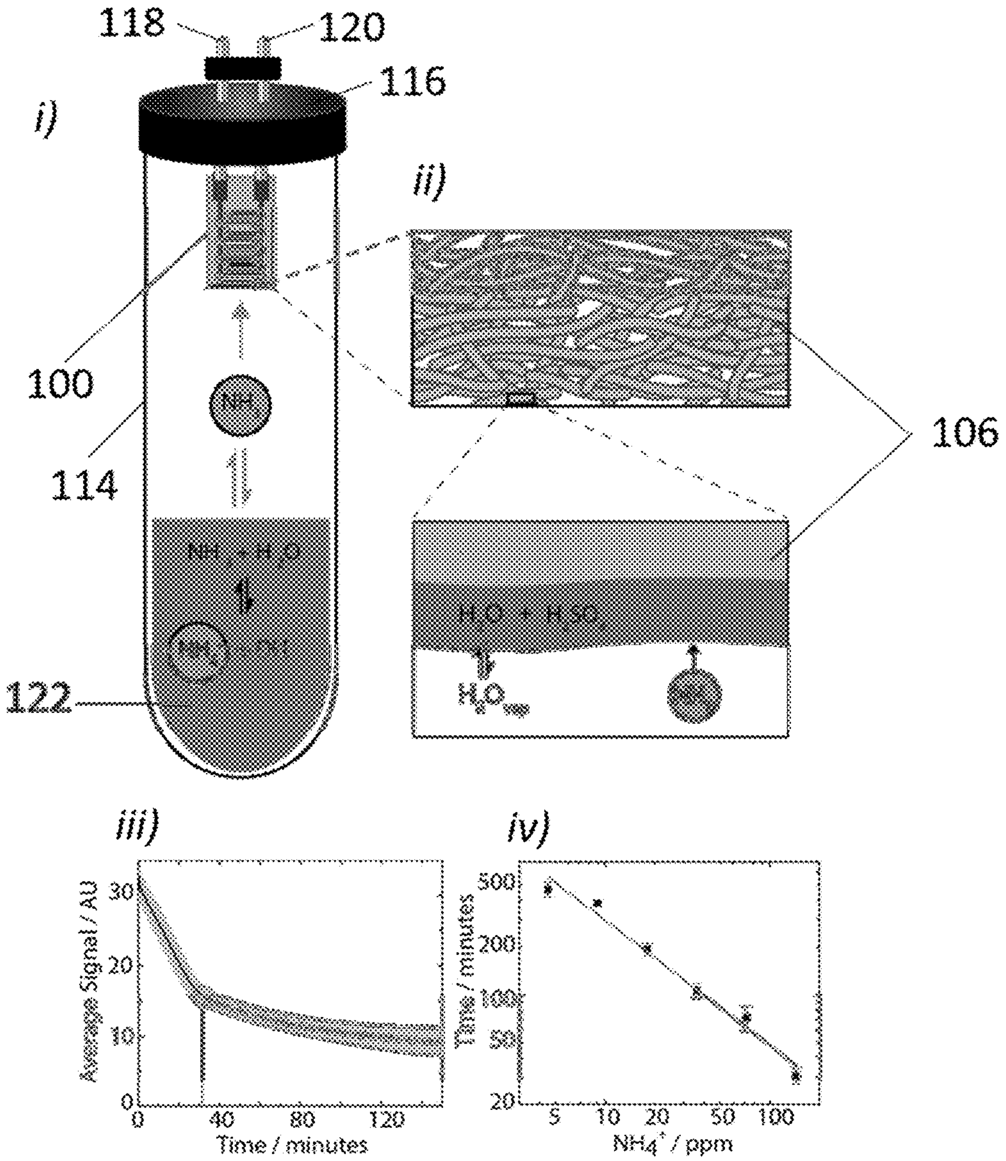
FIG. 3 illustrates a device for determining a quantity of ammonium ions in soil sample extract.
Figure 10:
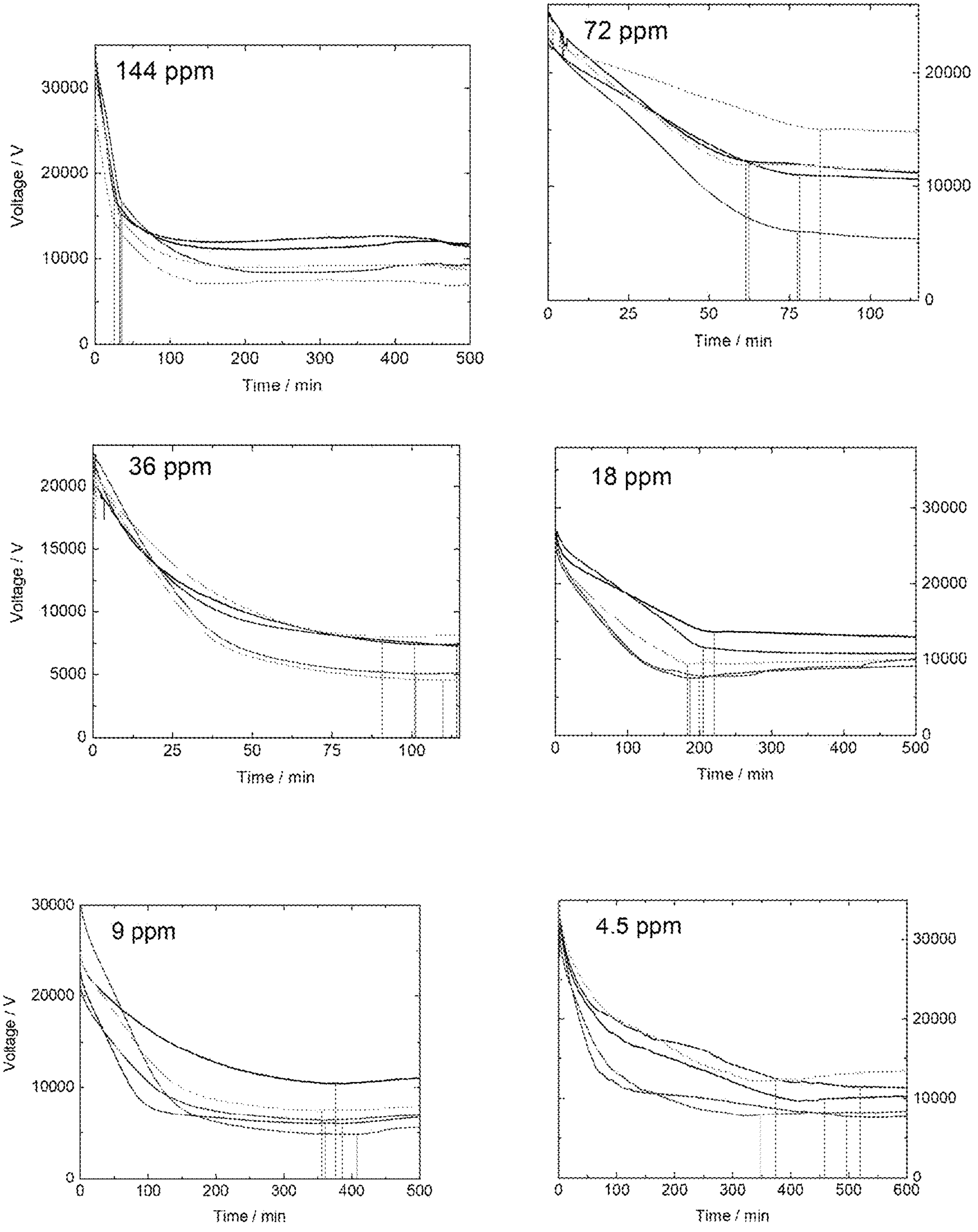
FIG. 10 illustrates raw data showing decrease in ionic conductivity (measured as a voltage), as sulphuric acid in a paper scrubber is neutralized by ammonia gas.
Figure 11:
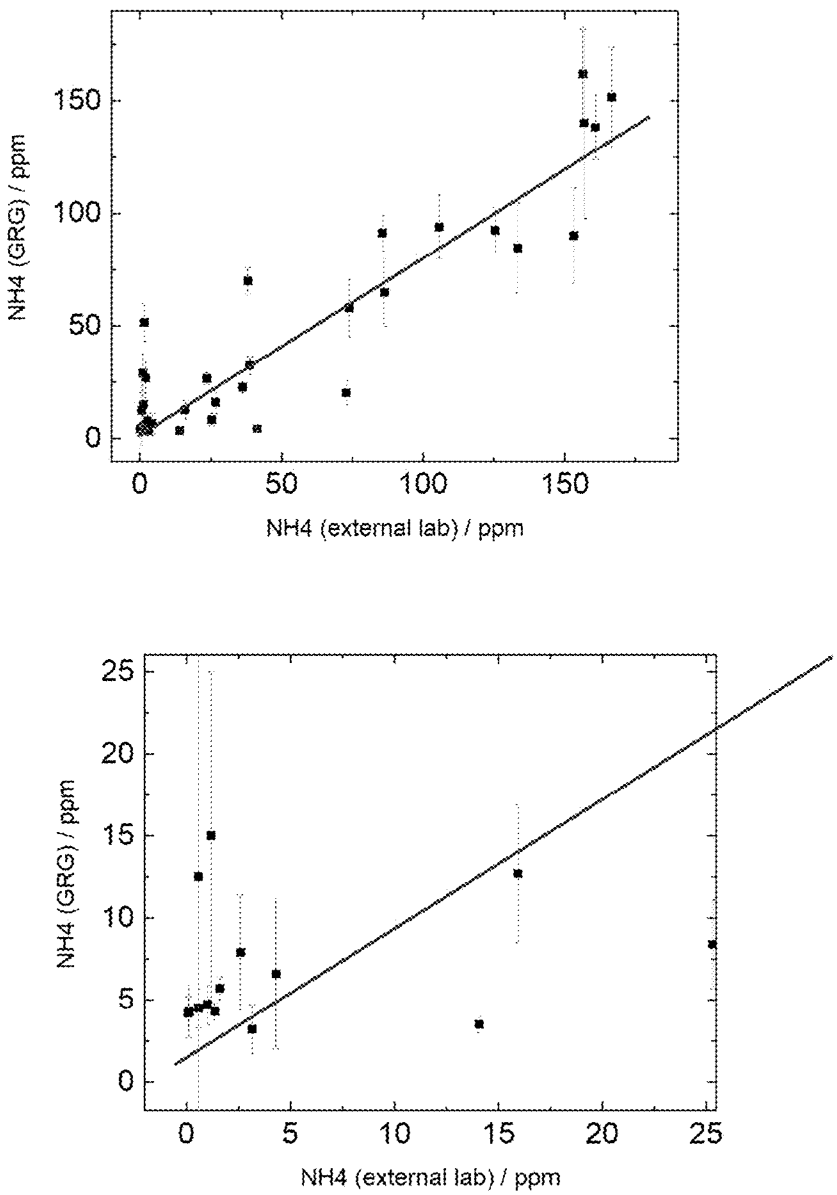
FIG. 11 illustrates soil-ammonium measurements made in soil fertilized in a variety of weather conditions.

With reference to FIG. 11, after calibration shown in FIG. 3.*iv* with data from FIG. 10, 35 soil-$NH_4^+$ measurements were made in soil fertilized with in for a variety of weather conditions (see FIG. 6). Soil-$NH_4^+$ measurements from the inventors' gas-phase $NH_4^+$ sensor (GRG) compared to external laboratory measurements with a score of $R^2$=0.85.

Figure 7:
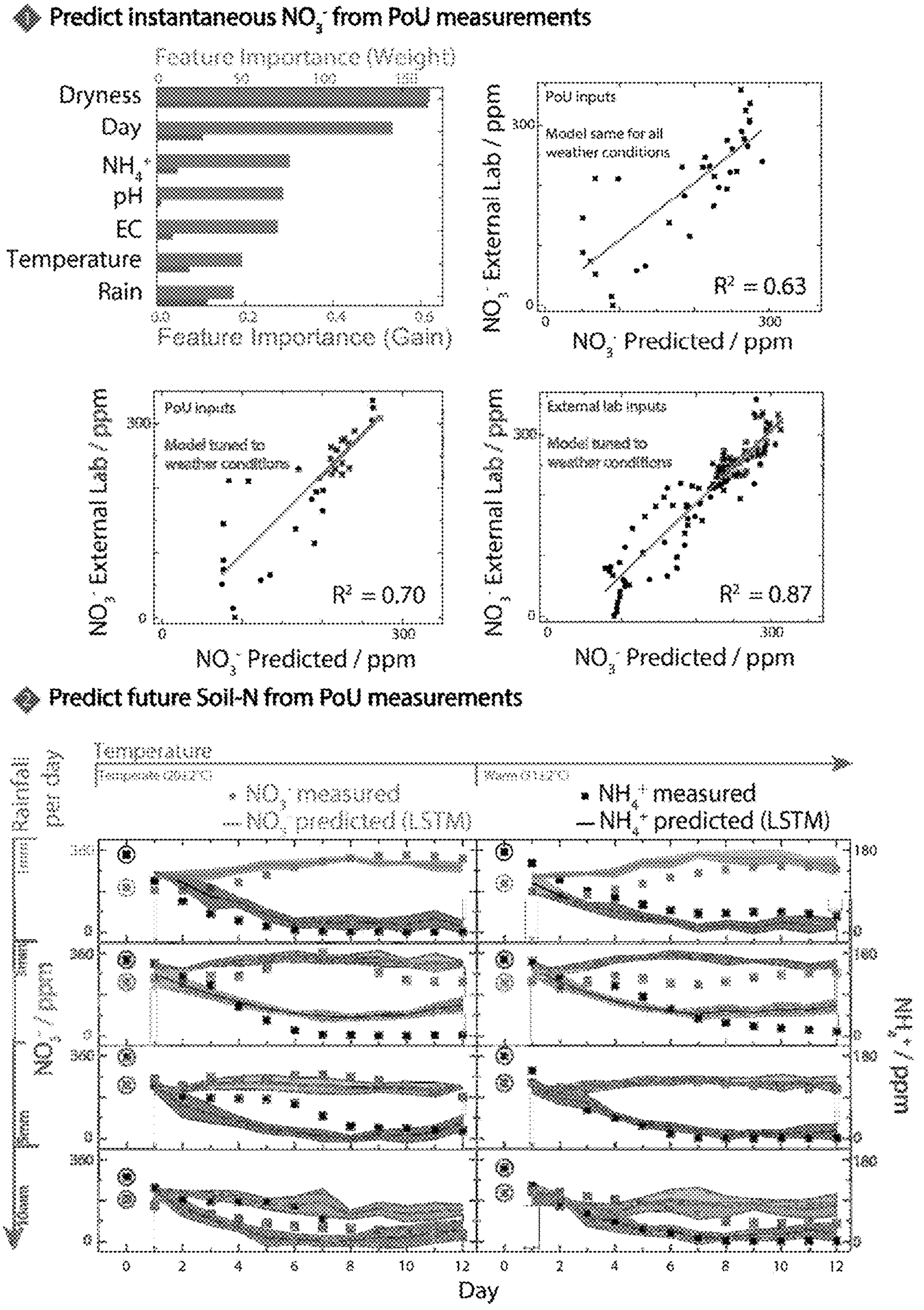
FIG. 7 illustrates machine learning models to estimate soil nitrate levels and forecast them into the future.
Figure 13:
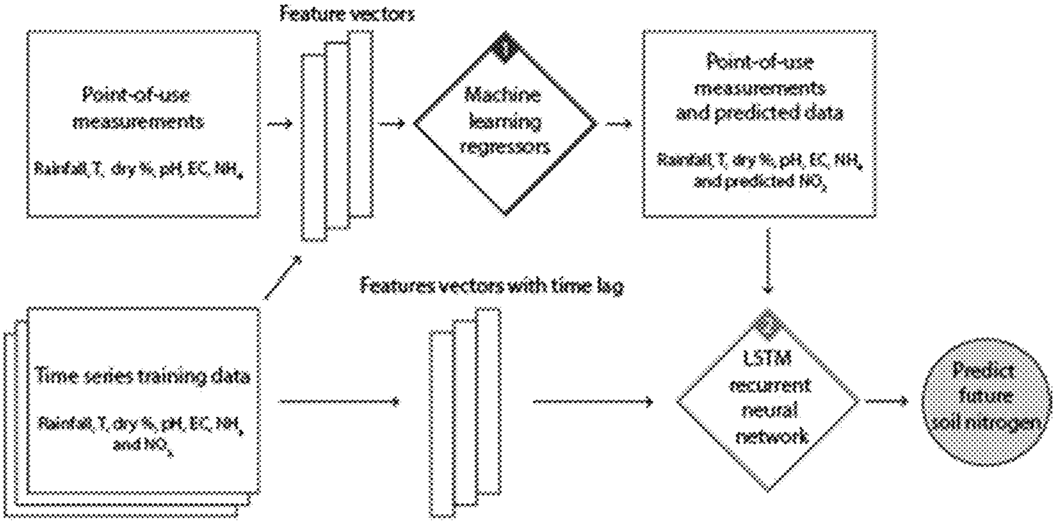
FIG. 13 illustrates prediction of the level of nitrate in soil instantaneously, using supervised machine learning, and both ammonium and nitrate into the future.
Figure 15:
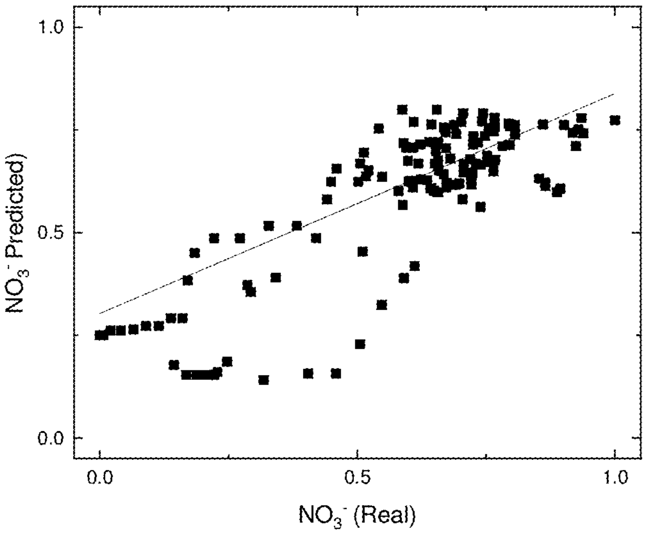
FIG. 15 illustrates the process of FIG. 7.1 (bottom left) with test inputs from an external lab rather than the inventors' lab.
Figure 16:
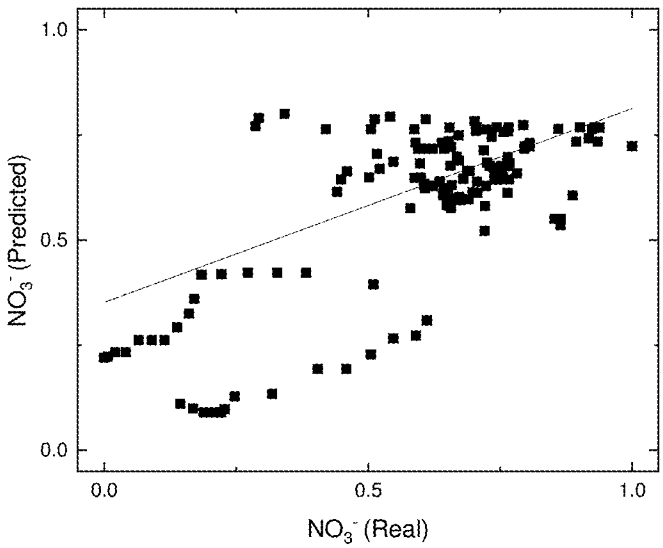
FIG. 16 illustrates prediction of nitrate using a K-nearest-neighbours algorithm.

Using supervised ML, the inventors attempted to predict the level of $NO_3^-$ in soil instantaneously, and both $NH_4^+$ and $NO_3^{31}$ into the future (see FIG. 13 for the ML prediction process flow). The measurements performed by the external laboratory (FIG. 6) were used as a training set. The performance of the model was then tested either with data from the external lab or data generated by the POU sensors in the inventors' lab as inputs. Training data matching the same environmental conditions (temperature and rainfall) as the test inputs were removed, so the model was always tested on unseen environmental conditions. Features were ranked in order of importance (by XGBoost, FIG. 7.1 top left), where soil dryness, time since fertilization and $NH_4^+$ were the most important. Combinations of features, regressors and tuning parameters were compared exhaustively (by grid search) to find the best general regressor to estimate the levels of $NO_3^-$ instantaneously (see FIG. 14 for $R^2$ scores for each set of environmental conditions). It was determined that the K-nearest-neighbours (Knn) algorithm, trained on all 7 features with tuning parameters of k=14, leaf size=1 and p=1, can predict instantaneous levels of $NO_3^-$ with $R^2$=0.63 using external lab results for training and the inventors' lab POU sensors for test input (FIG. 7.1 bottom left). Using the same model, but with external lab results as test inputs, removes the impact of inaccuracy from the inventors' lab sensors, resulting in $R^2$=0.68 (FIG. 15). It was also determined that XGBoost regressor produced the best predictions for dryer soils and Knn for wetter. Taking the inventors' lab POU sensors as test inputs, and the optimal regressor and tuning for each set of environmental condition offers even better performance, giving an optimised score of $R^{av}$=0.70 (score averaged across each set of environmental conditions—FIG. 7.1 bottom left). The same process, but with external lab results as test inputs, produces on optimized score of $R^2_{av}$=0.87 (FIG. 7.1 bottom right). This score for predicting levels of $NO_3^-$ in soil is comparable to direct measurements using optical ($R^2$=0.83; Fourier-transform infrared spectroscopy) or electrochemical methods ($R^2$=0.96; ion selective electrodes) as reported in the literature.[24,34] This result was pleasantly surprising given that no additional hardware was required for determining levels of $NO_3^-$ with high accuracy. The inventors also tuned a Knn model (k=11, leaf size=3, p=1) to predict levels of $NO_3^-$ in soil using only the most basic inputs—days since fertilization, rainfall and temperature (i.e. requiring no soil sensors at all) which yielded $R^2$=0.54 (FIG. 16).

With reference to FIG. 13, machine learning models trained with readily available environmental data and POU measurements enable prediction of difficult-to- measure soil nitrogen instantaneously with machine learning regressors (1). Prediction into the future is then enabled by treating data as time series in a LSTM neural network (2).

The following steps were taken to predict instantaneous soil-$NO_3^-$ (FIG. 13.1) Feature selection: Features ranked for predicting $NO_3^-$ calculated by weight and gain using XGBoost—see FIG. 7.1. Combinations are tested starting with all 7 features, then only 6 most important features, then the most important 5, down to the single most important feature The following steps were taken to predict soil-$NH_4^+$ and soil-$NO_3^-$ 1-12 days into the future (FIG. 13.2)

Figure 14:
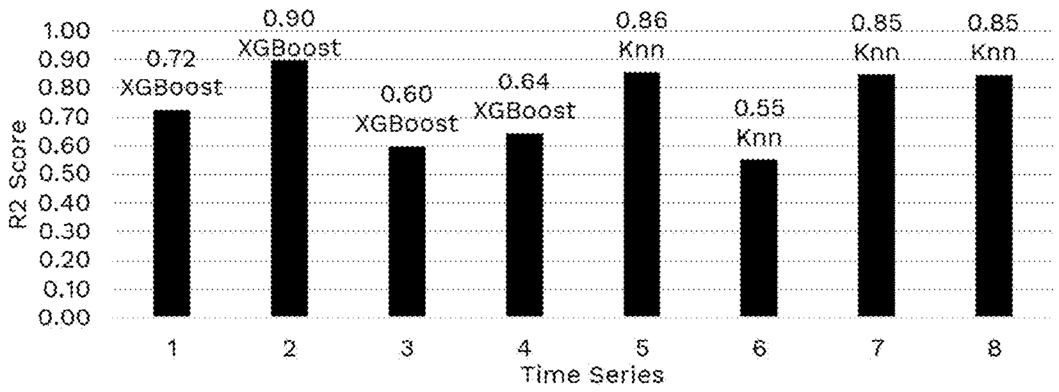
FIG. 14 illustrates $R^2$ scores for sets of environmental conditions to find a general regressor to estimate levels nitrate.

With reference to FIG. 14, each time series 1-8 (corresponding to soil under different environmental conditions, by controlling rainfall and temperature—see FIG. 6) was sequentially removed from the data, and predicted using the remaining data. Testing all combinations of features, regressors and tuning parameters results in a best-case prediction score for each time series, shown in FIG. 14. XGBoost is gives the best predictions for dryer soils and Knn for wetter soils. Poorer $NO_3^-$ predictions at moderate (3-5 mm) rainfalls, where $NO_3^-$ levels were relatively constant over time. The number of features (n_features), regressor and optimal tuning parameters for each time series are listed below.

With reference to FIG. 15, the same process was followed as for FIG. 7.1 (bottom left), with the same tuning parameters (k=14, leaf size=1, p=1), but test inputs were from the external lab rather than POU sensors from the inventors' lab, thus removing any impact of inaccuracy from the inventors' lab. The resulting score is $R^2$=0.68 (compared to the $R^2$=0.63 with inventors' lab inputs).

With reference to FIG. 16, Knn predicts $NO_3^-$ using a model tuned (k=11, leaf size=3, p=20) to only the most basic inputs—days since fertilization, rainfall and temperature (i.e. requiring no soil sensors at all.) with $R^2$=0.54. One model was used for all environmental conditions.

Figure 17:
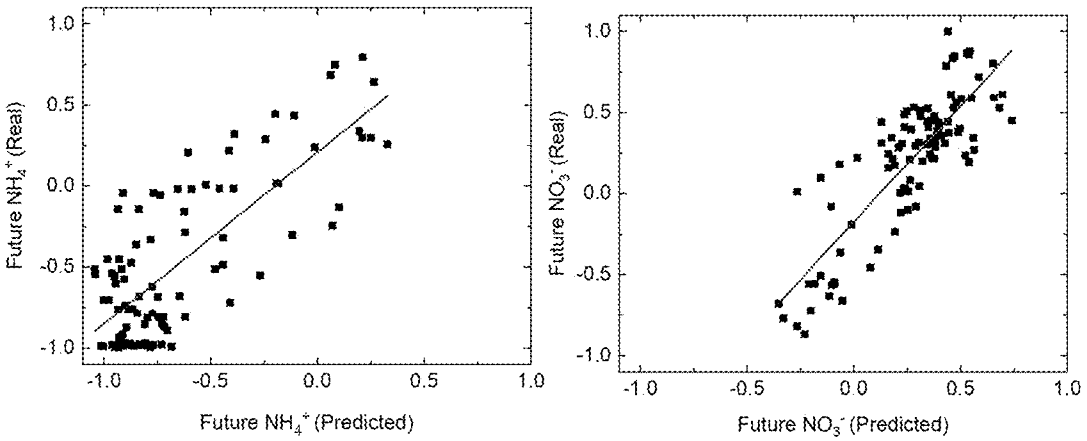
FIG. 17 illustrates the $R^2$ score for data in FIG. 7.2, showing soil-$NH_4^+$ and soil-$NO_3^-$ predicted by LSTM ML model 1-12 days into the future.

Although determining the concentration of $NH_4^+$ and $NO_3^-$ in soil at any given moment is important (as described above), from an operational point of view, it would also be useful to know what the levels of soil nitrogen (i.e. $NH_4^+$ and $NO_3^-$) will be in the future from a single measurement to create a precise schedule for future fertilization. Soil, however, introduces a memory effect: nutrient levels today depend on the nutrient levels and other factors from yesterday (property X and time t will be a function of X at t−1). Forecasting of soil-N into the future must, therefore, consider time and sequence of data, and possess a degree of memory, for multiple correlated features. Using the time-series dataset generated by the external lab, a long short-term memory recurrent neural network (LSTM) model (another supervised ML algorithm) was trained to forecast $NH_4^+$ and $NO_3^-$ into the future for unseen environmental conditions. The model was tuned using grid search, minimizing root-mean-squared error using time lag and model hyperparameters (training epochs, batch size, number of neurons). The optimal tuning was time lag=1, epochs=50, batch size=3 and number of neurons=3. The dataset was first concatenated into one multivariate time series. Each time series was then removed sequentially, and the model trained to predict the removed time series from the remaining data. Models were retrained for each desired forecast time (1-12 days into the future). Predictions for longer time periods were distorted by subsequent time series in the concatenation. Comparing predicted to real values over the 12-day period gives a score of $R^2_{NH4+}$=0.64 and $R^2_{NO3-}$=0.70 using only the initial concentrations for $NH_4^+$ and $NO_3^-$ on Day 0 which demonstrates efficacy with even the limited training dataset (FIG. 7.2, with $R^2$ plots in FIG. 17). In essence, by measuring $NH_4^+$, EC and pH in the field and gathering other environmental data from public sources, levels of $NO_3^-$ can be estimated for today and both levels of $NH_4^+$ and $NO_3^-$ into the future.

With reference to FIG. 7, low-cost POU measurements and machine learning models were used to estimate crucial, difficult-to-measure, parameters in complex systems, then forecast them into the future. $NO_3^-$ was predicted with instance based and ensemble learning regressors. Features were first ranked by importance to the XGBoost model, calculated by weight (number of times the feature occurs in the trees) and gain (each feature's contribution to each tree), shown in FIG. 7.1 (top left). Dryness is highly correlated with rainfall and temperature and can be predicted from temperature and rainfall using linear regression with $R^2$=0.86 (FIG. 12), without requiring further analytical measurements. There are unique environmental conditions for each time series (by controlling rainfall and temperature). Each time series was sequentially removed from the complete dataset, before training a model with the remaining dataset to make predictions for the removed set of environmental conditions. The trained model then gave instantaneous predictions for $NO_3^-$ using only test inputs from POU sensors in the inventors' lab (temperature, rainfall, calculated dryness, time since fertilization, EC, pH and $NH_4^+$). Optimal feature combinations, regressors and tuning parameters were compared using grid search. Data processing steps are described in more detail in the SI. The best performing regressor for all environmental conditions is Knn, which predicts $NO_3^-$ using only POU sensors from the inventors' lab as test inputs with $R^2$=0.63 (FIG. 7.1 top right). Optimizing the model for each set of environmental conditions (regressor and tuning for each shown in FIG. 14) improves the score to $R^2$=0.70 (FIG. 7.1 bottom left). Using external lab data as test inputs (removing any inaccuracy from the inventors' PoU sensors) gave optimized predictions for $NO_3^-$ with $R^2$=0.87 (FIG. 7.1 bottom right). The dataset was then used to train a LSTM-RNN model to forecast $NH_4^+$ and $NO_3^-$ into the future, also for unseen environmental conditions (FIG. 7.2). Each time series was removed sequentially, and the model trained on the remaining data. Feature time lag and model hyperparameters (training epochs, batch size, number of neurons) were tuned to optimize forecasting. Models were retrained for each desired forecast time (1-12 days into the future) and comparing predicted to real values over the 12 day period gives a score of $R^2_{NH4+}$=0.64 and $R^2_{NO3-}$=0.70.

Figure 12:
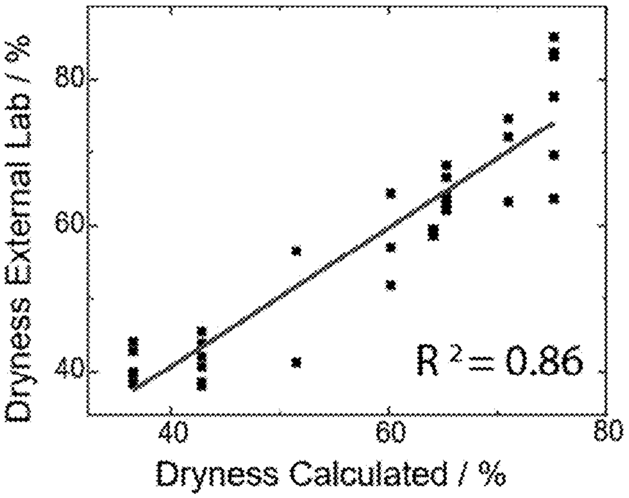
FIG. 12 illustrates correlation of dryness with rainfall and temperature.

With reference to FIG. 12, in the dataset, dryness is highly correlated with rainfall and temperature. Dryness can be predicted using linear regression with $R^2$=0.86 using the equation below, and hence can be estimated using these two metrics without needing further analytical measurements.

FIG. 17 illustrates $R^2$ score for data in FIG. 7.2, showing soil-$NH_4^+$ and soil-$NO_3^-$ predicted by LSTM ML model 1-12 days into the future. The LSTM ML model was poorer at predicting lower soil-$NO_3^-$ levels and higher soil-$NH_4^+$ levels.

In accordance with the above, it is possible to estimate the levels of hard-to-measure chemicals in soil using easily accessible soil/climate data and ML models. This entirely new strategy allows determining and predicting levels of nitrogen ($NH_4^+$ and $NO_3^-$) in soil, both instantaneously and into the future. The inventors have produced the first soil nitrification dataset that provides enough temporal resolution (~3 day measurement frequency), for a range of conditions, to train a ML model. The strength of the present approach is that it primarily uses, inexpensive/easily accessible tools for the soil measurements (pH and EC meter with the exception of a new paper-based, gas-phase $NH_4^+$ sensor developed in this work) and publicly available weather data (rainfall and temperature; in this study the inventors simulated weather in a controlled manner) to estimate the levels of soil nitrogen through ML. The method presented is remarkably high performance such that concentration of instantaneous soil-$NO_3^-$ can be estimated using PoU inputs with $R^2_{av}$=0.70, and using laboratory inputs with $R^2_{av}$=0.87 (comparable to existing high performance $NO_3$ sensors) without the need for additional hardware. Using a LSTM model, the levels of $NH_4^+$ and $NO_3^-$ can also be forecast 12 days into the future, for unseen environmental conditions, with $R^2_{NH4+}$=0.64 and $R^2_{NO3-}$=0.70. Furthermore, the paper-based, disposable, gas-phase $NH_4^+$ sensors (i.e. chemPEGS of the third embodiment above) developed in this work could also be used alone at the PoU without the ML model or other sensors if instantaneous detection of $NH_4^+$ is needed alone. The approach presented in this work may have the following three potential weaknesses:

- The supervised ML algorithms used for the prediction of soil-N require a training dataset, meaning prior measurements/climate data are needed to make the estimation algorithms work. This problem could partially be resolved by using data for soil nitrogen already published in the literature to create a training dataset. A training dataset could also be created using the PoU sensor toolkit described in this work in addition to occasional measurements of soil-$NO_3^-$ in an external laboratory. It is expected that performance of the algorithms will increase over time as more data are generated using the sensors and laboratory measurements. The LSTM approach also concatenated all training data into one long multivariate time series, resulting in a model that would only predict cyclical patterns if allowed to predict longer times than the length of the input time series (t≥16 days). This problem may be addressed by treating each set of environmental conditions as panel data (with separate multivariate time series for PoU measurements in different locations/environmental conditions), linking between panels and training over longer time periods.
- chemPEGS (for measuring $NH_4^+$ at the PoU) may be cross-sensitive to other alkaline gases and currently takes a long time to perform a measurement; 30-450 minutes for 144-4.5 ppm $NH_4^+$. chemPEGS, however, demonstrated sufficient performance for measuring soil-$NH_4^+$ as it is most sensitive to $NH_{3(g)}$ due to its high water solubility. The time it takes to produce a result could also be reduced by measuring the rate of change during neutralization or training a predictive machine learning model on short measurement times. The sensitivity of chemPEGS could also be improved by using a lower concentration of $H_2SO_4$.[35,36]
- The dataset generated is limited (sparse) and does not include various scenarios such as sudden changes in weather, different types of soils and fertilizers (e.g., urea). The current work also does not include crops, which would draw nitrogen from the soil and affect nitrogen dynamics. Further work is needed to create a model to predict nitrogen uptake by plants.

The impact of this work is that growers can instantly determine crucial soil nutrients using only point-of-use measurements and weather data, and forecast nutrients into the future to build better fertilization plans. This would ensure that appropriate nutrients are present, when needed, by the crops. This approach could enable precision farming of a new calibre (with significantly lowered capital investment), reducing fertilizer requirements, soil degradation and eutrophication, while improving crop yields. Furthermore, it is hoped this approach will extend to complex media other than soil, where simple chemical measurements and easily accessible data, combined with machine learning, can be used to predict, and forecast crucial outputs in healthcare, food and environmental monitoring.

Soil experiments: Top soil with sandy loam texture (69% sand 2.00-0.063 mm diameter, 25% silt 0.063-0.002 mm diameter, 6% clay <0.002 mm diameter, density 774 g/l measured in NRM Laboratories, part of Cawood Scientific, United Kingdom) was purchased from Westland and used in the experiments without further modifications. For the soil experiments performed in the inventors' laboratory, the water-soluble compounds and small particles were extracted from the soil samples by mixing 100 ml di$H_2O$ with 100 g of soil, and pressing with a potato press (VonShef). The solution extracted was used in the subsequent, pH, EC and $NH_4^+$ measurements in the inventors' laboratory. Soil samples (200 g), for the measurements at the external laboratory (NRM), were extracted from the soil pots and stored in a Ziploc bag (placed inside a cool box along with cooling element) which were collected and analysed within 2 days. Different to the inventors' method of handling, the external lab used a soil-to-water ratio of 1:2.5 as they dried the samples before processing to improve consistency (this was not done, which caused issues surrounding unmatching results between the external measurements and measurements performed by the inventors' group). Levels of soil nitrogen were measured colorimetrically by the external laboratory. $NH_4^+$ was reacted with alkaline hypochlorite and phenol to form indophenol blue. Sodium nitroprusside acted as a catalyst in formation of indophenol blue which was measured at 640 nm. $NO_3^-$ was reduced to nitrate using cadmium in an open tubular cadmium reactor. A diazo compound formed between nitrite and sulphanilamide, which was coupled with N-(1-Napthyl)ethylenediamine dihydrochloride to give a red azo dye, measured at 540 nm. For all soil experiments, soil was weighed into pots of 5.1 kg, and fertilized with 51 ml 0.665 M (12,000 ppm) $NH_4NO_3$ while mixing thoroughly, resulting in soil at approximately 120 ppm $NH_4NO_3$.

Control of rainfall and temperature: Rainfall was fixed at 1, 3, 5, or 10 mm/day, implemented by adding a daily equivalent (pots were watered every 2 days) of 57 ml, 172 ml, 286 ml and 573 ml respectively to a pot area of 573 $cm^2$. Temperature was controlled by wrapping pots containing soil with nichrome wire (purchased from Amazon) and applying a 36 V potential, resulting in an electrical current of 1.5 A supplied from two Tenma 72-8350A power supplies in series. Soil temperature was measured at 3 points (centre, edge and in between) and averaged to estimate the temperature of soil periodically, using a Silverline 469539 Pocket Digital Probe Thermometer.

Measurement of EC and pH of soil: Using a Hanna Instruments HI5222-type benchtop EC/pH meter, the pH and EC of the solution extracted from the samples of soil were measured. Each sample was measured five times and the readings were averaged to reduce error.

Machine learning model: All computational work was performed using Python (3.6) in PyCharm integrated development environment. For modelling and optimization, the following core packages were used: Keras API for Tensorflow (LSTM model), Scikit-learn (ensemble and Knn regressors), XGBoost, pandas and NumPy.

The following references, cited above, are incorporated by reference.

[1] United Nations, *World Population Prospects* 2019, 2019.
[2] R. Mosheim, *United States Dep. Agric.—Econ. Res. Serv.* 2019.
[3] N. Alexandratos, J. Bruinsma, *Land use policy* 2012, DOI 10.1016/S0264-8377(03)00047-4.
[4] R. N. Tetteh, 2015, 6, 301.
[5] K. T. Osman, *Soil Degradation, Conservation and Remediation,* 2014.
[6] V. H. Smith, G. D. Tilman, J. C. Nekola, in *Environ. Pollut.,* 1999.
[7] F. Zheng, D. Zhu, M. Giles, T. Daniell, R. Neilson, Y. G. Zhu, X. R. Yang, *Sci. Total Environ.* 2019, DOI 10.1016/j.scitotenv.2019.04.384.
[8] Q. Wang, M. Ma, X. Jiang, D. Guan, D. Wei, B. Zhao, S. Chen, F. Cao, L. Li, X. Yang, J. Li, *Appl. Soil Ecol.* 2019, DOI 10.1016/j.apsoil.2018.12.019.
[9] J. F. Rosas, *Card Work. Pap.* 2012.
[10] J. Melkonian, H. Van Es, A. Degaetano, J. Sogbedji, L. Joseph, *Proc. Symp. Integrating Weather Var. into Nitrogen Recomm.* 2007.
[11] Q. Zhu, J. P. Schmidt, H. S. Lin, R. P. Sripada, *Geoderma* 2009, DOI 10.1016/j.geoderma.2009.10.004.
[12] J. F. Shanahan, N. R. Kitchen, W. R. Raun, J. S. Schepers, *Comput. Electron. Agric.* 2008, DOI 10.1016/j.compag.2007.06.006.
[13] N. Tremblay, Y. M. Bouroubi, C. Bélec, R. W. Mullen, N. R. Kitchen, W. E. Thomason, S. Ebelhar, D. B. Mengel, W. R. Raun, D. D. Francis, E. D. Vories, I. Ortiz-Monasterio, *Agron. J.* 2012, 104, 1658.
[14] C. Cilia, C. Panigada, M. Rossini, M. Meroni, L. Busetto, S. Amaducci, M. Boschetti, V. Picchi, R. Colombo, *Remote Sens.* 2014, DOI 10.3390/rs6076549.
[15] N. R. Kitchen, K. A. Sudduth, S. T. Drummond, P. C. Scharf, H. L. Palm, D. F. Roberts, E. D. Vories, *Agron. J.* 2010, DOI 10.2134/agronj2009.0114.
[16] M. L. Stone, J. B. Solie, W. R. Raun, R. W. Whitney, S. L. Taylor, J. D. Ringer, *Trans. Am. Soc. Agric. Eng.* 1996, DOI 10.13031/2013.27678.
[17] S. M. Sze, K. K. Ng, J.-P. Colinge, C. A. Colinge, *Phys. Semicond. Devices* 2006, i.
[18] H. J. Kim, J. W. Hummel, S. J. Birrell, *Trans. ASABE* 2006.
[19] R. Shaw, R. M. Lark, A. P. Williams, D. R. Chadwick, D. L. Jones, *Agric. Ecosyst. Environ.* 2016, DOI 10.1016/j.agee.2016.06.004.
[20] T. Hengl, J. G. B. Leenaars, K. D. Shepherd, M. G. Walsh, G. B. M. Heuvelink, T. Mamo, H. Tilahun, E. Berkhout, M. Cooper, E. Fegraus, I. Wheeler, N. A. Kwabena, *Nutr. Cycl. Agroecosystems* 2017, 109, 77.
[21] B. Zaman, M. McKee, *Open J. Mod. Hydrol.* 2014, 04, 80.
[22] C. Brewster, I. Roussaki, N. Kalatzis, K. Doolin, K. Ellis, *IEEE Commun. Mag.* 2017, DOI 10.1109/MCOM.2017.1600528.
[23] K. L. Tully, R. Weil, *Commun. Soil Sci. Plant Anal.* 2014, 45, 1974.
[24] J. Choosang, A. Numnuam, P. Thavarungkul, P. Kanatharana, T. Radu, S. Ullah, A. Radu, *Sensors* (Switzerland) 2018, 18, DOI 10.3390/s18103555.
[25] R. Burton, "Nitrate Sensing in the Soil," can be found under https://www.cambridgeconsultants.com/insights/nitrate-sensing-in-the-soil, 2016.
[26] R. Shaw, A. P. Williams, A. Miller, D. L. Jones, *Agric.* 2013, DOI 10.3390/agriculture3030327.
[27] G. Barandun, M. Soprani, S. Naficy, M. Grell, M. Kasimatis, K. L. Chiu, A. Ponzoni, F. Güder, *ACS Sensors* 2019, DOI 10.1021/acssensors.9b00555.
[28] F. Beeckman, H. Motte, T. Beeckman, *Curr. Opin. Biotechnol.* 2018, DOI 10.1016/j.copbio.2018.01.014.
[29] J. M. Stark, M. K. Firestone, *Appl. Environ. Microbiol.* 1995, 61, 218.
[30] L. T. T. Nguyen, Y. Osanai, I. C. Anderson, M. P. Bange, M. Braunack, D. T. Tissue, B. K. Singh, *Plant Soil* 2018, 426, 299.
[31] A. E. Taylor, A. T. Giguere, C. M. Zoebelein, D. D. Myrold, P. J. Bottomley, *ISME J.* 2017, 11, 896.
[32] T. Hao, Q. Zhu, M. Zeng, J. Shen, X. Shi, X. Liu, F. Zhang, W. de Vries, *J. Environ. Manage.* 2020, 270, 110888.
[33] J. L. Smith, J. W. Doran, *Soil Sci. Soc. Am.* 1996, 169.
[34] N. Rogovska, D. A. Laird, C. P. Chiou, L. J. Bond, *Precis. Agric.* 2019, 20, 40.
[35] N. Albilal, Nanomaterials for Pregnancy Detection, Imperial College London, 2014.
[36] M. Grell, C. Dincer, T. Le, A. Lauri, E. Nunez Bajo, M. Kasimatis, G. Barandun, S. A. Maier, A. E. G. Cass, F. Güder, *Adv. Funct. Mater.* 2018, DOI 10.1002/adfm.201804798.

It will be appreciated that the above description is made by way of example and not limitation of the scope of the appended claims, including any equivalents as included within the scope of the claims. Various modifications are possible and will be readily apparent to the skilled person in the art. Likewise, features of the described embodiments can be combined with any appropriate aspect described above and optional features of any one aspect can be combined with any other appropriate aspect.

The invention claimed is:

1. A gas sensor for determining a quantity of target ions in a sample by sensing a target gas, the gas sensor comprising:
- first and second electrodes;
- a support layer between the first and second electrodes;
- a reagent on the support layer for binding the target gas and a container for receiving the sample;
- wherein the first and second electrodes are in electrical contact with the support layer and the reagent;
- wherein the container is fluidically connected to the first and second electrodes;
- wherein the container contains or is fluidically connected to the reagent for converting the target ions in the sample into the target gas;
- wherein an inside of the container and gas sensor are sealed;
- wherein the first and second electrodes are in a headspace of the container;
- wherein the support layer is not in direct contact with the sample; and
- wherein the first and second electrodes are configured to measure an electrical impedance of the support layer.

2. The gas sensor of claim 1, further comprising a voltage source, wherein the voltage source is configured to apply an electrical potential between the first and second electrodes.

3. The gas sensor of claim 1, wherein the target gas is an alkaline gas and the reagent is acidic.

4. The gas sensor of claim 3, wherein the target gas is ammonia.

5. The gas sensor of claim 1, wherein the target ions in the sample are alkylammonium ions, fluoride ions, chloride ions, bromide ions, iodide ions or bicarbonate ions.

6. The gas sensor of claim 3, wherein the target gas is an alkyl amine.

7. The gas sensor of claim 1, wherein the target gas is an acidic gas and the reagent is alkaline.

8. The gas sensor of claim 7, wherein the target gas is carbon dioxide, hydrogen fluoride, hydrogen chloride, hydrogen bromide or hydrogen iodide.

9. The gas sensor of claim 7, wherein the target gas is hydrogen fluoride, hydrogen chloride, hydrogen bromide or hydrogen iodide.

10. The gas sensor of claim 1, wherein the target ions in the sample are ammonium ions, alkylammonium ions, fluoride ions, chloride ions, bromide ions, iodide ions or bicarbonate ions.

11. The gas sensor of claim 10, wherein the sample is soil, agricultural runoff, river water, sea water, sewage, blood, urine, an extract of soil, an extract of agricultural runoff, an extract of river water, an extract of sea water, an extract of sewage, an extract of blood, or an extract of urine.

12. The gas sensor of claim 1, wherein the sample is soil, agricultural runoff, river water, sea water, sewage, blood, urine, an extract of soil, an extract of agricultural runoff, an extract of river water, an extract of sea water, an extract of sewage, an extract of blood, or an extract of urine.

13. The gas sensor of claim 1, wherein the reagent for converting the target ions in the sample into the target gas is an acidic or basic solution.

14. The gas sensor of claim 1, wherein the sample is soil extract, the target ions are ammonium ions and the container contains a sodium hydroxide solution.

15. The gas sensor of claim 1, wherein the sample is sewage, blood, urine, an extract of sewage, an extract of blood, or an extract of urine.

* * * * *